(12) United States Patent
Vayser et al.

(10) Patent No.: US 8,596,847 B2
(45) Date of Patent: *Dec. 3, 2013

(54) FILM ILLUMINATION SYSTEM

(75) Inventors: Alex Vayser, Mission Viejo, CA (US);
Kenneth B. Trauner, San Francisco, CA (US); Thomas L. Grey, San Marcos, CA (US)

(73) Assignee: Invuity, Inc., San Francisco, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/366,140

(22) Filed: Feb. 3, 2012

(65) Prior Publication Data
US 2012/0136216 A1 May 31, 2012

Related U.S. Application Data

(63) Continuation of application No. 12/750,581, filed on Mar. 30, 2010, now Pat. No. 8,132,949, which is a continuation of application No. 11/818,090, filed on Jun. 12, 2007, now Pat. No. 7,686,492.

(60) Provisional application No. 60/813,391, filed on Jun. 13, 2006.

(51) Int. Cl.
*A61B 1/32* (2006.01)
*A61B 1/07* (2006.01)

(52) U.S. Cl.
USPC .................. 362/572; 362/574; 600/212

(58) Field of Classification Search
USPC .............. 362/572, 573, 574, 556, 558, 804; 600/212, 517, 574
See application file for complete search history.

(56) References Cited

U.S. PATENT DOCUMENTS

| | | | |
|---|---|---|---|
| 3,638,644 A | 2/1972 | Reick | |
| 3,641,332 A | 2/1972 | Reick et al. | |
| 3,890,960 A | 6/1975 | Wunsch et al. | |
| 4,226,228 A | 10/1980 | Shin et al. | |
| 4,562,832 A | 1/1986 | Wilder et al. | |
| 4,592,344 A | 6/1986 | Scheer | |
| 4,597,030 A | 6/1986 | Brody et al. | |
| 4,605,990 A | 8/1986 | Wilder et al. | |

(Continued)

FOREIGN PATENT DOCUMENTS

EP 0101781 A1 3/1984
GB 2078526 A 1/1982

OTHER PUBLICATIONS

International search report and written opinion dated Jan. 29, 2008 for PCT/US2007/013829.
Office action dated Apr. 9, 2009 for U.S. Appl. No. 11/818,090.

(Continued)

*Primary Examiner* — Bao Q Truong
(74) *Attorney, Agent, or Firm* — Wilson, Sonsini, Goodrich & Rosati (57) ABSTRACT

An illuminator film system may include one or more pre-cut sections of optical film applied to a waveguide to allow light to exit the waveguide through the film in a predetermined manner. The one or more pre-cut sections may be removed and reapplied during a procedure to redirect the light. A laminated illuminator film may be provided that uses a laminated optical film structure to direct light from a fiber optic input. Such a laminated illuminator film may be very low profile, low cost and easy to apply to a retractor for providing illumination during a surgical procedure.

15 Claims, 7 Drawing Sheets

(56) References Cited

U.S. PATENT DOCUMENTS

| | | |
|---|---|---|
| 4,643,172 A | 2/1987 | Taff et al. |
| 4,697,578 A | 10/1987 | Burgin |
| 4,807,599 A | 2/1989 | Robinson et al. |
| 4,842,356 A | 6/1989 | Mori |
| 4,961,617 A | 10/1990 | Shahidi et al. |
| 5,035,232 A | 7/1991 | Lutze et al. |
| 5,353,786 A | 10/1994 | Wilk et al. |
| 5,355,284 A | 10/1994 | Roberts |
| 5,807,261 A | 9/1998 | Benaron et al. |
| 6,185,356 B1 | 2/2001 | Parker et al. |
| 6,504,985 B2 | 1/2003 | Parker et al. |
| 7,306,559 B2 | 12/2007 | Williams |
| 7,686,492 B2 * | 3/2010 | Vayser et al. ............ 362/572 |
| 8,132,949 B2 * | 3/2012 | Vayser et al. ............ 362/572 |
| 2003/0169603 A1 | 9/2003 | Luloh et al. |
| 2004/0221375 A1 | 11/2004 | Douglas |
| 2007/0208226 A1 | 9/2007 | Grey et al. |
| 2007/0293729 A1 * | 12/2007 | Grey et al. ............ 600/212 |
| 2008/0002426 A1 | 1/2008 | Vayser et al. |

OTHER PUBLICATIONS

Office action dated Jul. 1, 2011 for U.S. Appl. No. 12/750,581.

\* cited by examiner

FILM ILLUMINATION SYSTEM

CROSS-REFERENCES TO RELATED APPLICATIONS

The present application is a continuation of U.S. patent application Ser. No. 12/750,581 now U.S. Pat. No. 8,132,949, filed Mar. 30, 2010, which is a continuation of U.S. patent application Ser. No. 11/818,090 now U.S. Pat. No. 7,686,492, filed Jun. 12, 2007, which claims priority from U.S. Provisional Patent Application No. 60/813,391 filed Jun. 13, 2006, the full disclosures of which are incorporated herein by reference.

BACKGROUND OF THE INVENTION

1. Field of the Invention

The inventions described below relate to the field of medicine and more specifically, to providing body cavity illumination for use in medical, dental and veterinary procedures.

2. Background of the Invention

Existing technology for illumination during surgical/medical procedures is often limited to overhead illumination. This illumination comes from either overhead lighting or head mounted fiber optic systems. Traditional overhead lighting systems face numerous limitations. Direct exposure of the field from the overhead source is required. Changes in patient or surgeon positioning requires repositioning of the light source. Frequent adjustments provide an inconvenience for the surgeon and disrupt the surgical flow. For deeper cavities, overhead systems provide poor quality illumination. Positioning of the surgeon, or the instruments may shield the overhead lighting and prevent illumination from reaching the field of the procedure.

Head mounted fiber optic systems are used frequently for more limited surgical exposures, however, these devices also have numerous drawbacks. First, the surgeon is tethered by the light cord attached to the headset, limiting mobility in the operating room. Second, the devices are associated with head and neck fatigue with frequent or more prolonged use. Third, the devices require the surgeon to maintain a steady head and neck position to provide a constant and steady illumination of the field. Fourth, the use of remote light sources and fiber bundles introduces tremendous inefficiencies into the system. A six-foot fiber optic cable may lose 65% of the incoming light from a light source. The headlamp optical components may lose another 60% of the light from the fiber optic cable. In addition, surgeons using head mounted systems frequently complain of the heat generated by such systems.

In addition, both headlamp and overhead systems provide inadequate illumination when used with less invasive surgical procedures with a limited incision to access a deeper or broader surgical cavity. For these cases, both overhead and headlamp systems only illuminate a fraction of the volume of the surgical space.

The introduction of minimally invasive surgical techniques, has raised the demand for delivery of high intensity light through minimal surgical incisions into deep surgical fields. To address this demand, light delivery devices have been developed for delivery of light from remote, high intensity light sources to the surgical field. These devices generally consist of bundles of optical fibers that are integrated with or directly adhere to surgical retractors to illuminate the field and are connected via fiber optic cable to a high intensity light source. While these devices provide a way to illuminate the surgical field, they provide highly inefficient illumination. The small bundle diameter is susceptible to being completely blocked by any surgical debris or splatter such as blood or tissue, thereby requiring constant cleaning to maintain illumination. In addition, due to the limited divergence angle and highly Gaussian intensity profile, these devices only provide a small spot of light that requires constant repositioning to view the entire surgical area. In addition, these fiber optic light pipes are very expensive to manufacture, requiring significant amounts of expensive human labor.

Waveguide illuminators are known in the art and typically allow light to exit the illuminator by using optical structures molded into the surface of the waveguide itself. Light injected into such waveguides is typically contained in the waveguide through total internal reflection. When the light strikes the optical structures, the reflection angle is interrupted such that the light now refracts out of the waveguide. Such systems may be useful for illumination of deep tissues, but often require the use of expensive, specialized tooling or manufacturing processes. Moreover, these waveguides are rigid and must be designed to fit particular instruments so different waveguides must be available to accommodate the variety of surgical instruments used in a given surgical procedure.

Still other applications may involve woven fiber optic strands or fiber optic strands cut at various lengths to generate diffuse lighting. Light escapes the fiber either through a nick in the surface of the fiber or because a material has been applied to the surface of the fiber that disrupts total internal reflection, or the light merely escapes out of the cut ends of the fiber. This type of diffuse illumination is typically not suitable for illumination of deep tissues because it provides an insufficient level of illumination for tissues of interest and often shines light back into the surgeon's eyes, making viewing of the tissues difficult. Such systems are also expensive to manufacture.

BRIEF SUMMARY OF THE INVENTION

Light in medical applications may be used for illumination, diagnostic or therapeutic purposes. While this disclosure discusses primarily illumination applications, diagnostic and therapeutic applications are understood to be included as well.

A film illumination system may include one or more pre-cut sections of optical film applied to a waveguide to allow light to exit the waveguide through the film in a predetermined manner. The one or more pre-cut sections may be removed and reapplied during a procedure to redirect the light. A laminated illuminator film may be provided that uses a laminated optical film structure to direct light from a fiber optic input. Such a laminated illuminator film may be very low profile, low cost and easy to apply to a retractor for providing illumination during a surgical procedure.

In an illumination technique according to the present disclosure, a small, pre-shaped section of film is applied to the surface of a waveguide to allow light to exit the waveguide in a predetermined manner substantially only from the area to which the pre-shaped section of film is applied. Said pre-shaped section of film becomes a simple, stick-on illuminator film when applied to the waveguide or light guide. This pre-shaped section of film should have an area that is significantly smaller than the surface area of the waveguide or light guide on to which the pre-shaped or pre-cut section has been placed.

A film illumination system according to the present disclosure may comprise one or more pre-cut sections of optical film, the pre-cut film sections including optical structures, for example, prismatic structures, for directing or focusing or diffusing light entering one side of the film as it exits the opposite side of the film. Said pre-cut section may also include one or more tabs for handling the pre-cut section and for removeably placing the pre-cut section on to a plastic waveguide. Pre-cut optical film sections may also include an adhesive layer for adhering to the waveguide. The composition of the adhesive layer may be selected to provide a refractive index specifically designed to enhance the leakage of light from the waveguide especially if the indices of the optical film layer and the waveguide are similar.

Tabs may be color coded for the type of light directing function such as for example, diffuse, direction, focused, etc. The tab may also be used to show the directionality of a directional film. The waveguide may receive light from any suitable light source and may control and contain the light inside of the waveguide through total internal reflection. The waveguide may have polished surfaces and/or coated surfaces to promote internal reflection.

A user may apply a pre-cut section or stick-on illuminator film to the waveguide to allow light to exit the waveguide. The stick-on illuminator film may also be removed and reapplied to a different part of the waveguide and/or in a different orientation to direct light as desired. Multiple pre-cut sections may be applied to the same waveguide to create a desired illumination area.

For example, the waveguide or light guide may be a retractor made from a suitable light guiding material (e.g., acrylic, polycarbonate, silicone, glass, etc., that may be transparent or translucent) with a width greater than its thickness and a front surface that faces the surgical area. The light guide or waveguide may be a surgical instrument or may be attached to a surgical instrument. Two generally diffusing pre-cut sections may be placed near the lateral edges of the retractor up a desired distance from its tip to provide generally diffuse illumination of the surgical area, and a third pre-cut section may be placed between the first two pre-cut sections, said third pre-cut section providing a directional beam of light to illuminate a particular portion of the surgical area. The surgeon may perform some work, then move or rotate the directional pre-cut section to better illuminate another portion of the surgical area while keeping the other two diffuse precut sections in place. At the end of the procedure, the pre-cut sections may be removed from the plastic waveguide and discarded while the waveguide may be sterilized and reused. Damaged or occluded film sections may simply be removed and replaced. The user may employ any combination of stick-on illuminator films to achieve desired illumination. Pre-cut sections of a stick-on illuminator film may be provided at extremely low cost.

Alternatively, a laminated film illumination assembly may be formed from an optical fiber having a suitable connector end for attaching to light source or light guide cable and a free end that is laminated with at least two layers of optical film. The optical fiber may be supplied as a mono-fiber or as a bundle of optical fibers. In a preferred orientation, the optical fibers are placed at one of the narrow ends of a rectangular shaped laminate structure with enough of the free optical fibers held in the laminate structure to hold the fibers securely and reduce the likelihood that the fibers can be pulled out during normal use. Preferably, the bottom layer of the laminate structure has an inside surface that is reflective or that has optical structures that serve to reflect light toward the top layer. The bottom layer also has a suitable adhesive on the outside surface for attaching the assembly to a surgical instrument, for example, a retractor. The upper layer preferably incorporates optical structures that serve to diffuse, shape, focus and/or direct light coming into that layer. The space between the upper and lower films is preferably occupied by an air layer, but an intermediate light guide layer, e.g., a suitably thick acrylic film or a thin molded polycarbonate or silicone piece, may occupy this space to promote total internal reflection or the two films may be adhered together thereby eliminating any substantial air space wherein an adhesive may promote internal reflection. The laminated film section may be made to be more or less flexible by employing such materials, or the film may be treated or structured to promote or restrict flexibility. Another protective transparent film may be placed on the upper film to protect the optical structures. Light exits the free optical fibers at one end of the laminate structure, travels along the laminate structure and is eventually reflected off of the lower layer and through the upper layer where it is directed as desired to illuminate tissue for surgical, diagnostic or therapeutic purposes. The user merely attaches a light source, e.g., a fiber optic light guide cable connected to a xenon, halogen or LED light source, to the connector end, peels a release liner from the adhesive on the bottom layer and attaches the assembly to a surgical instrument, e.g., a metal retractor. At the end of the procedure, the user may discard the assembly because of its low cost. A laminated illuminator film may be made very thin due to the thinness of the optical fibers and films of which it is made. A thin illuminator may be attached to a retractor and not take up valuable space needed to perform the surgery. It may be made in different sizes, thereby making the illuminator suitable for many types of surgical instruments and many types of surgeries. For example, a flat rectangular shape may be suitable for flat instruments such as a retractor blade. Alternatively, the flat film laminate may be formed as a cylinder, e.g., by attaching the two ends of the rectangular shaped film laminate, to slip over a round instrument such as nerve root retractor. Other instrument geometries may be accommodated by suitably shaping the film laminate. Furthermore, because the material is very inexpensive and the assembly process can be substantially automated, a laminated illuminator film may be very inexpensive.

DETAILED DESCRIPTION OF THE INVENTION

Figure 1:
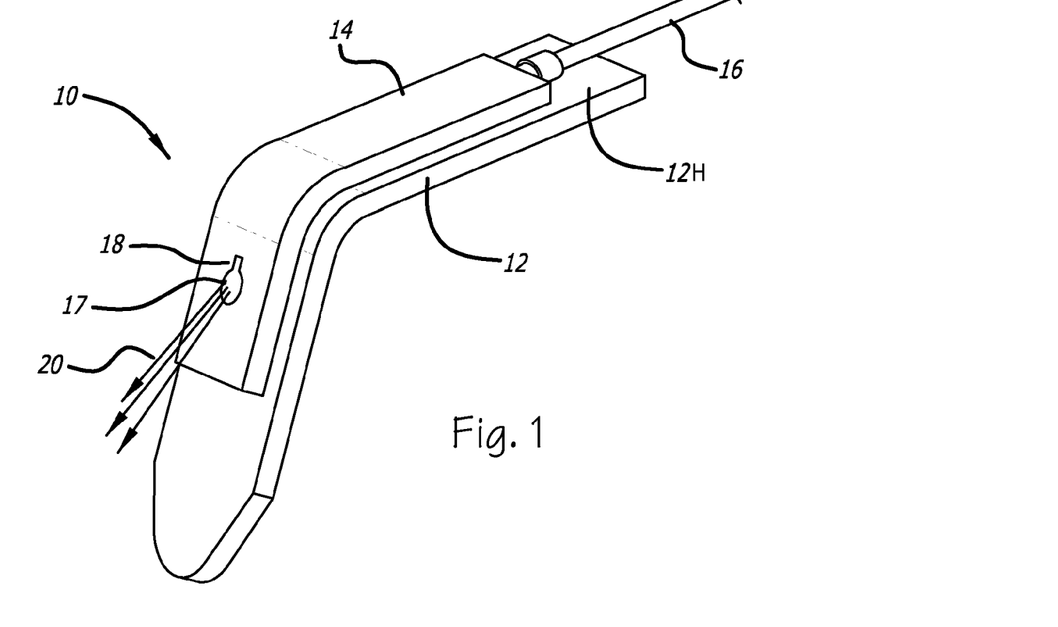
FIG. 1 is a perspective view of a surgical illumination system employing a pre-cut optical illuminator film.

Surgical illumination system 10 of FIG. 1 includes surgical retractor 12 with handle 12H, waveguide 14 and fiber optic light guide cable 16, which is attached to any suitable light source. Waveguide 14 functions to receive and conduct light from light guide cable 16 and the waveguide contains the light through total internal reflection. Without any surface interruptions, light energy contained in the waveguide would stay contained in the waveguide, subject to minor absorption, refraction and other losses as they occur over time. Stick-on illuminator film 17 is made from an optical film that changes the refractive index of the area of waveguide 14 to which the film is attached. Stick-on illuminator film 17 is provided with tab 18 to facilitate handling of the illuminator film. When stick-on illuminator film 17 is attached to waveguide 14, directional light 20 is allowed to escape and illuminate a surgical area of interest.

Waveguide 14 may be connected to an external light source, such as a xenon light source through fiber optic light guide cable 16, or it may have an integrated light source, such as an integrated LED including drive electronics and battery. Alternatively, waveguide 14 may be attached to a portable light source, such as a portable LED light source.

The shape of stick-on illuminator 17 may be any suitable shape and the shape geometry may be determined, at least in part, by the desired illumination target. For example, a circular precut section may be more suitable for a round illumination target and a rectangular precut section may be suitable for a wide angle illumination target. Such suitable illumination target geometries may be combined to create a combined illumination target. For example, a precut section may include a rectangular portion for providing a percentage of the available light for wide angle illumination and a circular portion for providing a percentage of the available light for spot illumination.

Figure 2:
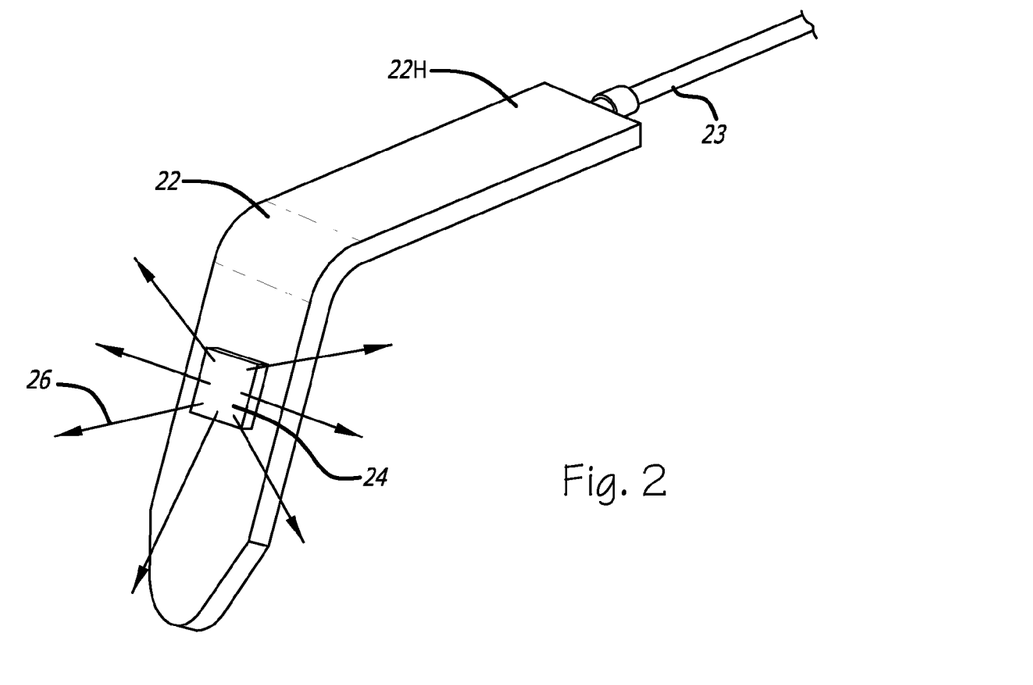
FIG. 2 is a perspective view of an alternate illuminator using pre-cut, stick-on film.

In an alternative configuration, waveguide retractor 22 of FIG. 2 serves as the mechanical retractor and the light waveguide and is attached to any suitable light source through fiber optic light guide cable 23. In this configuration, stick-on illuminator film 24 is not provided with a tab, and it also provides diffuse illumination 26 that may be suitable for illuminating a larger surgical area than stick-on illuminator film 17 of FIG. 1. In this instance, illumination 26 may be hemispherical, but it may be preferred to reduce the amount of light be reflected back up into a surgeon's eyes. Waveguide retractor 22 may be a rigid device formed of any suitable material, e.g., molded polycarbonate or acrylic, or may be a flexible device, e.g., molded silicone. Waveguide retractor 22 may be in any suitable shape, e.g., bar, tube, etc. and includes handle 22H.

Figure 3:
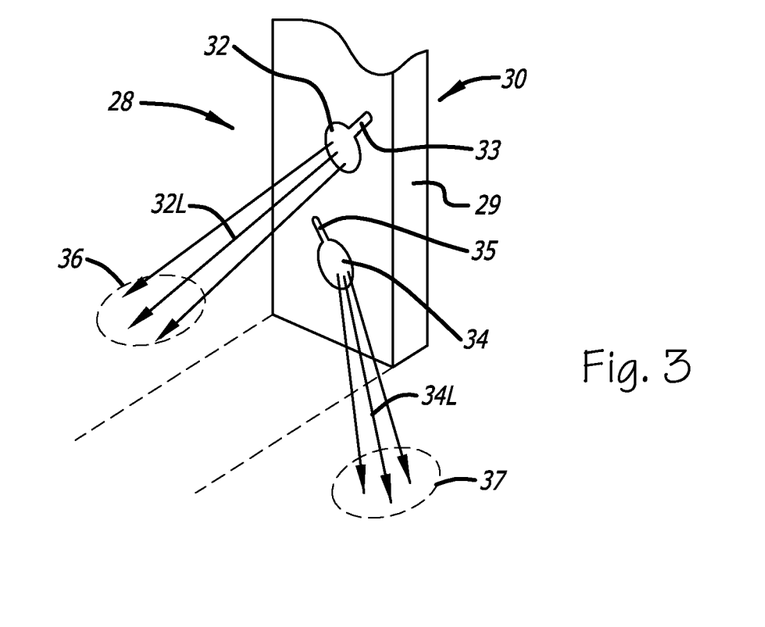
FIG. 3 is a close up view of pre-cut illuminator films with directional beams.

FIG. 3 provides a close-up view of surgical illuminator 28 showing distal end 29 of waveguide 30. Directional stick-on illuminator films 32 and 34 are shown with respective tabs 33 and 35 that also mark the direction of the respective directed light output 32L and 34L, i.e., the light output is in the direction opposite of the tabs. Tab 33 of stick-on illuminator film 32 is pointed to the right, indicating that the direction of illumination output 32L is to the left to illuminate area of interest 36 that is to the left of waveguide 30. Tab 35 of stick-on illuminator film 34 is pointed to the left, indicating that the direction of illumination output 34L is to the right to illuminate a particular area of interest 37 that is to the right of waveguide 30.

Figure 4:
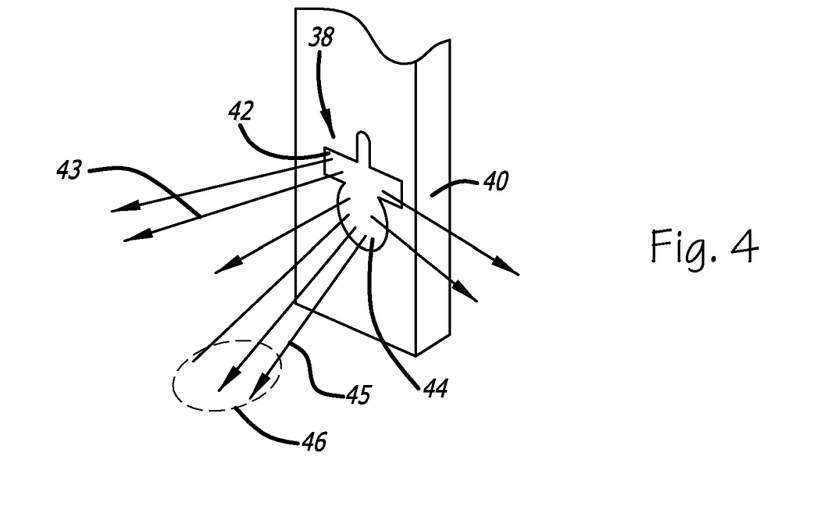
FIG. 4 is a close up view of pre-cut illuminator film with a combination diffuse and directional beam.

Referring now to FIG. 4, combination pre-cut illuminator film 38 incorporates diffuse and focused illumination features. Pre-cut, stick-on film element 38 is attached to a light conducting waveguide such as waveguide 40. Stick-on film element 38 has a diffuse light output portion 42 that creates diffuse light 43 to illuminate a general surgical area and has a directed light output portion 44 that creates directed light 45 that illuminates a specific surgical area such as area 46. Precut, stick-on film element 38 is fabricated using standard film converting techniques. Again, the user positions the waveguide, then applies the stick-on illuminator film, or the illuminator film may be pre-applied to the waveguide before positioning the waveguide into the surgical field. The diffuse output portion may be designed to provide any pattern of diffuse light, e.g., lambertian, planar, curved, etc. The directed output portion may be designed to provide any pattern of directed light, e.g., circular, polygonal, etc. The diffuse output portion may even be constructed using two or more directional optical films providing two or more directional illumination outputs, e.g., a circular spot of light to the right of the waveguide midline and a square spot of light to the left of the waveguide midline.

Figure 5:
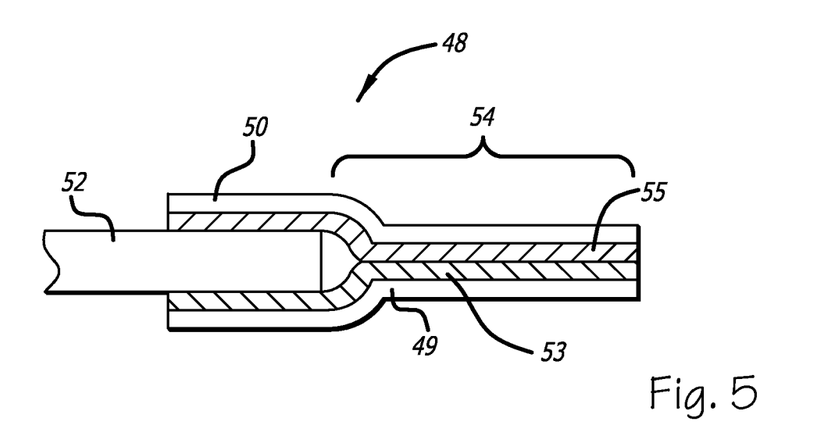
FIG. 5 is a cross-section of an optical fiber termination formed from optical films.

Optical termination 48 of FIG. 5 is formed of laminated optical film elements such as film elements 49 and 50 at the end of any suitable light guide such as fiber optic cable 52. Optical film 49 is illustrated as the lower portion with adhesive layer 53 and preferably serves a reflective function sending light to the upper portion. Optical film 50 is the transmissive upper portion with adhesive layer 55 and may operate in a focused light directing function or a light diffusing mode or both. In this configuration, adhesive layers 53 and 55 are thick enough and have sufficient optical clarity to allow light from fiber 52, which may be a fiber bundle or a fiber ribbon cable or other suitable arrangement of fibers, to propagate at least partially along the adhesive layers so that light exits substantially along output surface 54 of optical film 50 that extends beyond fiber 52.

Figure 5A:
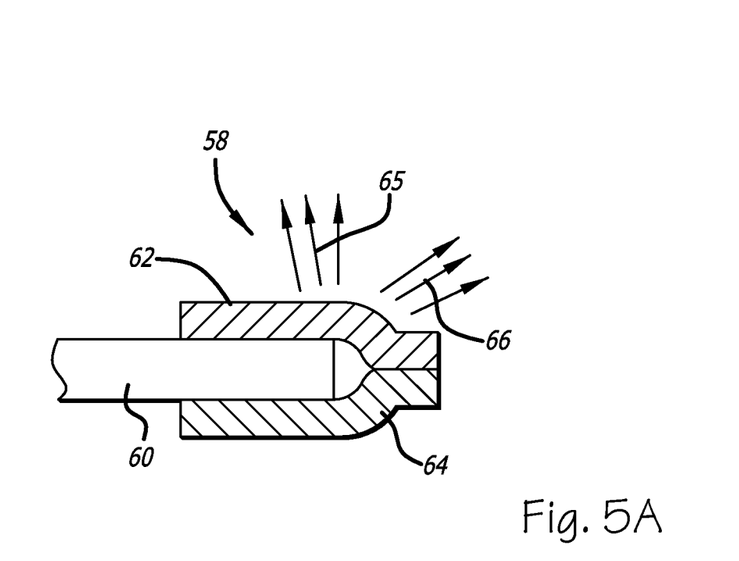
FIG. 5a is a cross-section of an alternative optical fiber termination formed from optical films.

If the adhesive layers are not so configured, then the film layers may be shortened as shown in FIG. 5A, showing alternative cable illuminator 58 which includes light cable 60, upper light directing film 62 and lower light reflecting film 64. Light exiting light cable 60 encounters lower reflecting film 64, causing the light to be directed toward upper light directing film 62, which may be configured to deliver diffuse light such as light 65, directed light such as light 66 or some combination thereof. Depending on the thickness of upper light directing film 62, the distribution of the light angles from light cable 60 and the paths that light rays take within the film laminate, some light may shine out the end of illuminator 58 and may actually shine downward direction past lower light reflecting film 64.

In an alternative configuration, lower light reflecting film 64 may be replaced with another piece of upper light directing film 62 to convert the highly Gaussian distributed light from light cable 60 to a more diffuse distribution that may be more useful in a diagnostic or therapeutic application or in an application where light shining in more than one direction is desired.

Figure 6:
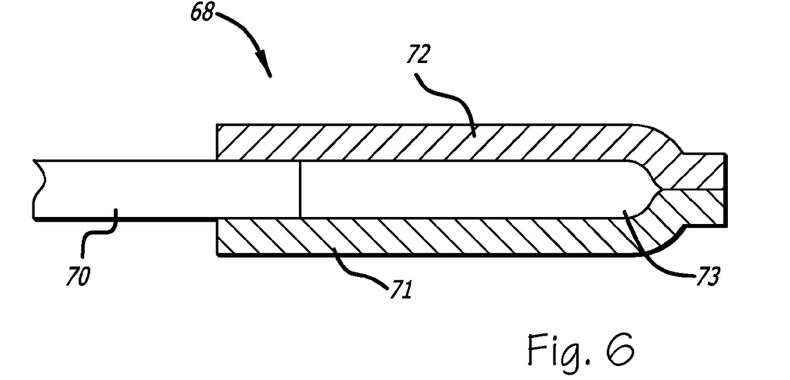
FIG. 6 is a cross-section of an optical fiber termination formed from optical films with an air gap.

Referring now to FIG. 6, laminated optical termination 68 is configured to engage any suitable light input structure such as an optical fiber bundle or a single core optical fiber or a length of polycarbonate, acrylic, silicone or other suitable light-conducting material such as light conduit or cable 70. Light reflecting film 71 directs light from light cable 70 above to light output film 72, which may provide diffuse illumination, directional illumination or a combination thereof. In this configuration, an air chamber such as air chamber 73 is created to allow all the light from light cable 70 above to be directed down the length of the optical film laminate structure created by joining films 71 above and 72 above along their edges. Films 71 above and 72 above are preferably cut in a rectangular shape, but may also be cut in any other suitable shape.

Figure 6A:
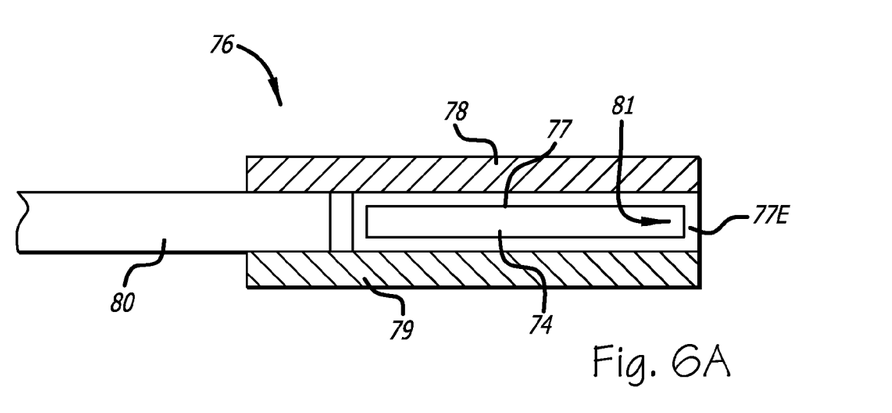
FIG. 6a is a cross-section of an alternative optical fiber termination formed from optical films with an air gap.

As shown in FIG. 6A, air chamber 74 of laminated optical termination 76 may be supported by a frame such as frame 77 made of a suitable material, e.g., plastic or metal, to help keep the air chamber open during use. Directing film 78 and reflecting film 79 perform the same function as the respective films in FIG. 6. Frame 77 may have a reflective surface at end 77E opposite of the light input from input cable 80 or may have a layer of reflective film 81 to help ensure that light only exits directing film 78.

Figure 7:
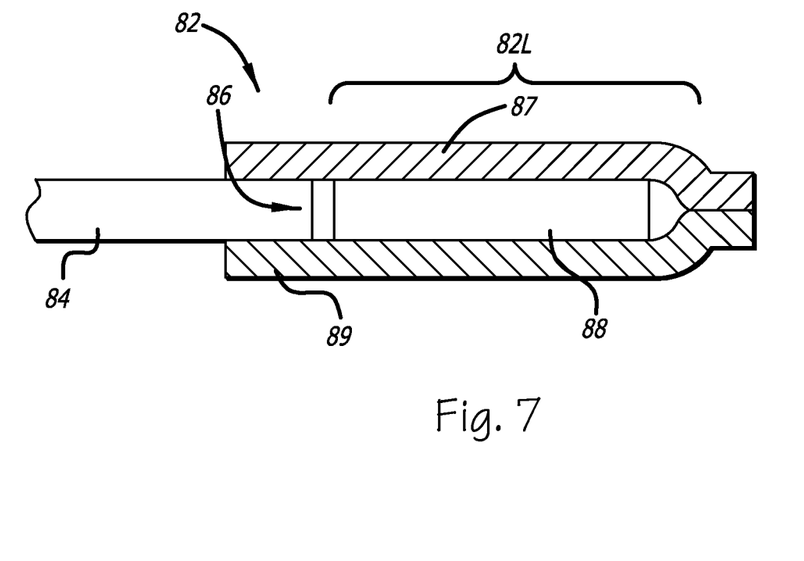
FIG. 7 is a cross-section of an optical fiber termination formed from optical films with a light guide section.

Referring now to FIG. 7, laminated film terminator 82 is sized to engage light input cable 84, which is preferably a fiber optic ribbon with the fibers generally planar in a side by side orientation. The ends of the fibers, ends 86, contact waveguide 88, which propagates light along the length 82L of the laminate structure. Reflecting film 89 serves to direct light toward output film 87. Termination waveguide 88 may be fabricated from any suitable optical material such as polycarbonate, acrylic or silicone or another layer of optical film. In this configuration, the thickness of termination waveguide 88 is at least the same thickness as light input cable 84 to help ensure that all light from light input cable 84 enters termination waveguide 88. Termination waveguide 88 may also incorporate optical structures, e.g., that are molded in or created via a hot stamp process that may help direct the light from light input cable 84 out to a surgical area to be illuminated.

Figure 8:
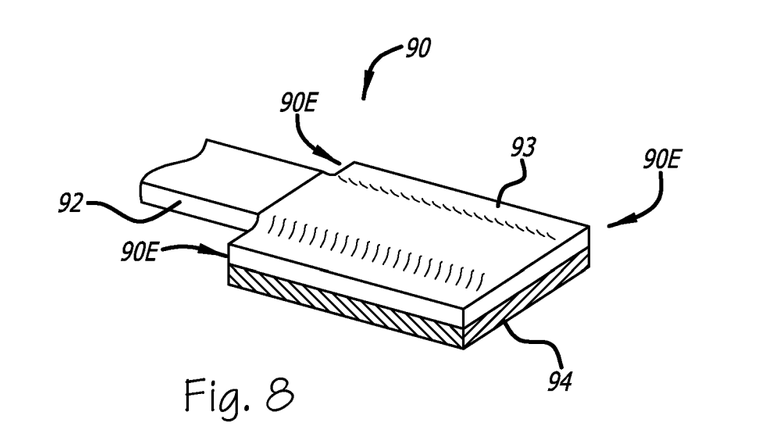
FIG. 8 is a perspective view of an illuminator assembly using a fiber optic ribbon cable and optical films.

Alternatively, a laminated film termination such as termination 90 of FIG. 8 engages a suitable light input element, for example, a fiber optic ribbon cable such as ribbon cable 92. Output or top film 93 and reflective or bottom film 94 are adhered together along terminator edges 90E. In this configuration, fiber optic ribbon cable 92 may have fibers extending the entire length of the laminated termination. In this case, the light may escape individual fibers where each fiber contacts top film 93 and/or bottom film 94, or the fibers may be nicked or otherwise treated to allow light to escape the fibers directly without the need to contact either the top film or the bottom film. Fiber optic ribbon cable 92 may be a bundle of fibers whose cut ends are arranged in a particular shape, e.g., the bundle may be round at the input connector and may be rectangular or some other shape at the film laminate end, it may be a ribbon cable where fibers are typically arranged side to side, or it may be a single core fiber.

Figure 9:
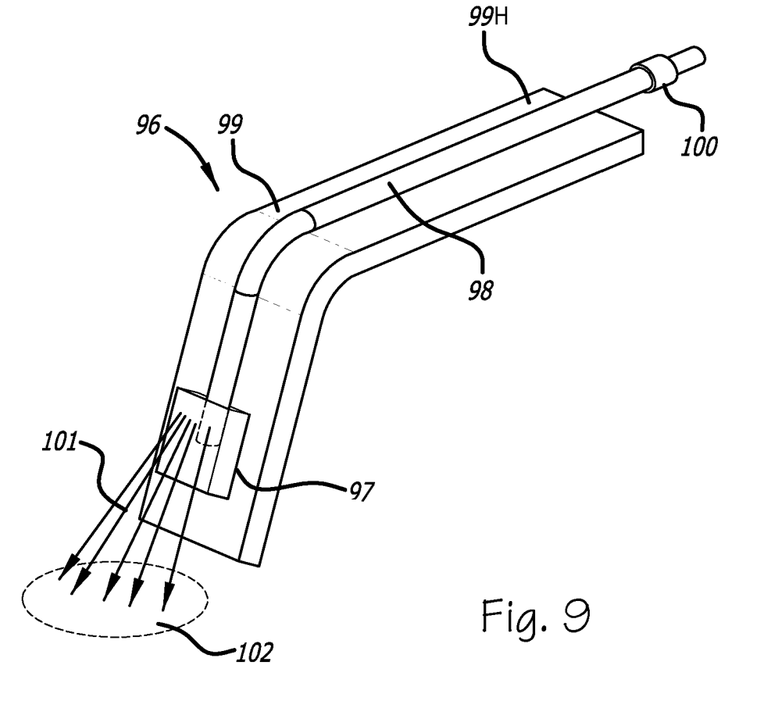
FIG. 9 is a perspective view of an optical film illumination assembly on a surgical retractor.

Laminated illuminator system 96 of FIG. 9 includes laminated film termination 97 on light input cable 98 attached to a retractor such as retractor 99 having handle 99H. Input connector 100 serves to connect the illuminator system to a source of light. Light input cable 98 conducts light from connector 100 to the film laminate structure 97, which directs light 101 to a surgical area 102 to be illuminated. Adhesive may be provided along light input cable 98 and/or film laminate structure 97 for attaching the illuminator film assembly to retractor 99.

Figure 10:
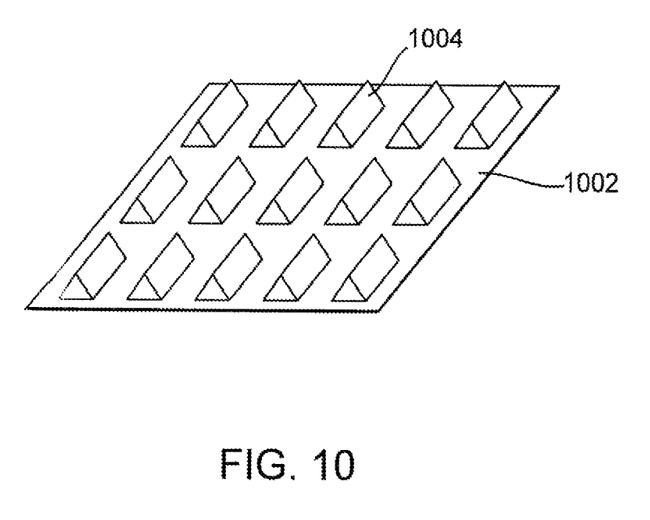
FIG. 10 illustrates prismatic structures on optical film.

A film illumination system according to the present disclosure may comprise one or more pre-cut sections of optical film, the pre-cut film sections including optical structures, for example, prismatic structures 1004, for directing or focusing or diffusing light entering one side of the film 1002 as it exits the opposite side of the film 1002.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A medical illuminator for illuminating a surgical field, said medical illuminator comprising:
    an optical waveguide conveying light therethrough by total internal reflection
    a light conduit conveying light from a light source to the waveguide; and
    one or more optical film pieces removably secured to the waveguide for extracting light from the waveguide through the optical film pieces and directing the extracted light to the surgical field, wherein the one or more optical film pieces each have an area smaller than the surface area of the optical waveguide.

2. The medical illuminator of claim 1, wherein the one or more optical film pieces further comprise:
    a light directing portion and a tab portion, wherein the orientation of the tab portion relative to the light directing portion indicates the direction of extracted light from the light directing portion.

3. The medical illuminator of claim 2, wherein the tab portion is color coded to indicate the degree of focus or directionality of the extracted light.

4. The medical illuminator of claim 1, further comprising an adhesive layer applied to the one or more optical film pieces for removably securing the one or more optical film pieces to the waveguide.

5. The medical illuminator of claim 4, wherein the adhesive layer performs index matching between the waveguide and the one or more optical film pieces.

6. The medical illuminator of claim 4, wherein the one or more optical film pieces may be removed from the waveguide and reapplied to a different position on the waveguide thereby redirecting light extracted therefrom.

7. The medical illuminator of claim 1, wherein the one or more optical film pieces further comprise:
    an optical film layer having at least one diffuse light directing portion; and
    at least one focused light directing portion.

8. The medical illuminator of claim 1, wherein the at least one optical film pieces extract diffuse light from the waveguide, and wherein another of the at least one optical film pieces extract focused light from the waveguide, the diffuse light and the focused light directed to the surgical field.

9. The medical illuminator of claim 1, wherein the at least one optical film pieces comprise optical structures for extracting the light from the waveguide.

10. The medical illuminator of claim 9. wherein the optical structures comprise prismatic structures.

11. The medical illuminator of claim 1, further comprising a retractor blade, wherein the waveguide is coupled with the retractor blade.

12. A method for illuminating a surgical field, said method comprising:
    providing an optical waveguide conveying light by total internal reflection;
    coupling a light conduit with the waveguide so that light from a light source is conveyed to the waveguide;
    applying one or more optical film pieces to the waveguide, wherein the one or more optical film pieces each have an area smaller than the surface area of the optical waveguide; and
    extracting light from the waveguide through the optical film and directing the extracted light to the surgical field.

13. The method of claim 12, wherein applying the one or more optical film pieces comprises adhesively attaching the one or more optical film pieces to the waveguide.

14. The method of claim 12, wherein the one or more optical film pieces comprise a light directing portion and a tab portion, the method further comprising orienting the tab portion relative to the light directing portion thereby indicating the direction of extracted light from the light directing portion.

15. The method of claim 12, wherein the one or more optical film pieces are color coded, the color code indicating the light directing function of the one or more pierces of optical film, and wherein applying the One or more optical film pieces comprises selecting the one or more optical film pieces based on the color coding.

\* \* \* \* \*